United States Patent [19]

Fulton, Jr.

[11] Patent Number: 5,043,356

[45] Date of Patent: Aug. 27, 1991

[54] COMPOSITION AND METHOD FOR REJUVENATING SKIN USING VITAMIN A PROPIONATE

[76] Inventor: James E. Fulton, Jr., 1236 Somerset La., Newport Beach, Calif. 92660

[21] Appl. No.: 467,794

[22] Filed: Jan. 19, 1990

[51] Int. Cl.$^5$ .................. A61K 31/22; A61K 31/34; A61K 31/08; A61K 31/05

[52] U.S. Cl. .................. 514/549; 514/473; 514/723; 514/731; 514/859; 514/863; 514/937; 514/947

[58] Field of Search ............... 514/537, 549, 473, 723, 514/859, 863, 937, 947, 731

[56] References Cited

U.S. PATENT DOCUMENTS

| | | | |
|---|---|---|---|
| 3,906,108 | 9/1975 | Felty | 514/560 |
| 4,532,133 | 7/1985 | Schmidt | 514/725 |
| 4,603,146 | 7/1986 | Kligman | 514/559 |
| 4,727,088 | 2/1988 | Scott et al. | 514/725 |

*Primary Examiner*—Richard L. Raymond
*Assistant Examiner*—Gary E. Hollinden
*Attorney, Agent, or Firm*—Poms, Smith, Lande & Rose

[57] ABSTRACT

Topically applied compositions for the accelerated rejuvenation of skin and an associated method of skin care treatment are disclosed utilizing vitamin A propionate of the general formula

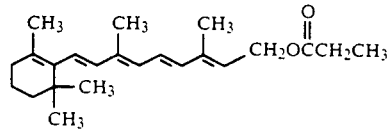

in an aqueous based carrier at a concentration ranging from 0.1% to 4.0%. The carrier may include non-ionic surfactants, preservatives and thickeners. The vitamin A propionate composition is topically applied to the skin at a frequency which is determined by skin type as determined by skin oil production rate.

8 Claims, No Drawings

COMPOSITION AND METHOD FOR REJUVENATING SKIN USING VITAMIN A PROPIONATE

BACKGROUND OF THE INVENTION

1. Field of the Invention

The present invention relates in a broad aspect to methods and compositions for the rejuvenation of human skin, treatment of skin disorders and for the general improvement in the quality and appearance of the skin. More particularly, the present invention is directed to treatment methodologies utilizing topically applied vitamin A propionate compositions to effectively retard and reverse the effects of photoaging of the skin and environmental damage and to treat acne without the unpleasant side effects associated with known vitamin A skin treatments. Other dermatological conditions effectively treated through the present invention include those linked to disorders of keratinization such as ichthyosis (hyperkeratosis), Darier's disease, acne, psoriasis and similar conditions. Also, vitamin A propionate is effective for treatment of early skin degeneration such as actinic keratosis, lentigos and melasma.

2. Description of the Prior Art

It is known that excessive sun exposure and general exposure to the environment causes anatomic degradation of human skin which is cumulative over time. The symptoms of such degradation are most pronounced on the face and around the eyes and are commonly manifested as wrinkles, blotchy discolorations, leathery skin texture, dryness, roughness, and premalignant growths. These symptoms are particularly apparent in light-skinned people who sunburn easily and in the elderly. Though skin has a natural ability to repair such damage, with aging the ability of the skin to spontaneously repair itself decreases. In addition, because the degradative effects of environmental exposure are cumulative over time, adults who have had excessive sun or environmental exposure in childhood may develop serious dermal alterations. Typically, such alterations remain microscopic long before the gross products of skin degradation noted above become visible. Then, in early adulthood, the degradation effects associated with such microscopic alterations are manifested as early aging of the skin.

Early efforts at treating human skin utilized vitamin A as a therapeutic agent. Vitamin A has been known since the 1940s to be an essential vitamin for the nutritional health of the skin. Early research showed the ability of vitamin A to stimulate new cell growth in the epithelium and to produce a softer and smoother skin appearance. In order to achieve these results, early skin treatment methodologies administered vitamin A internally, in large doses, usually in the form of the ester of palmitic acid, known as vitamin A palmitate. However, these vitamin A derivative treatments frequently resulted in hypervitaminosis-A toxic symptoms with such undesirable side effects as hair loss, migraine headaches, fatigue, and bone pain.

The beneficial effects of vitamin A in its acid form (retinoic acid) as a topical therapeutic agent are also well known in the art of dermatology. U.S. Pat. No. 3,729,568 discloses the repeated topical application of vitamin A acid to areas of the skin to clear the symptoms of acne. U.S. Pat. No. 4,603,146 discloses the beneficial effects of low strength applications of vitamin A acid in reportedly retarding the effects of aging on the skin. Such use of vitamin A acid in a maintenance therapy program reportedly results in a lightened skin, diminished wrinkling, and the disappearance of early sun-damaged spots such as actinic keratoses. Treatment with sufficient quantities of retinoic acid for therapeutic results, however, is known to cause visible irritation and inflammation of the skin. As a result, the skin exhibits an abnormal redness, or erythema, often followed by painful and unpleasant peeling of the skin which can be severe. Because these side effects are frequently difficult to tolerate by patients who otherwise would benefit from its use, retinoic acid as a skin treatment has limited applicability and must be carefully monitored. It must be dispersed with a physician's prescription.

It is known that vitamin A acid induces self-proliferation and new cell growth. Its effectiveness in the treatment of acne is related to this increase in the skin's regenerative capacity. Normally the turnover the skin takes 28 days for a new cell to form and shed off to the environment. Vitamin A acid reduces this regeneration time to between 10 and 15 days. As a result, the thickness of the uppermost layer of the skin, the epidermis, is doubled. The skin cell layer on the surface (stratum corneum) is reduced from 14 cell layers of impacted cells to eight or nine layers of loosely woven skin cells. There is also evidence that deeper down in the skin in the dermis there is new collagen formation as well as new blood vessel formation. The end result of this rapid regeneration is the peeling off of sun-damaged spots and an exfoliation of impactions of acne. There is also a gradual reduction in the fine lines and wrinkles.

Unfortunately, as noted above, a particular disadvantage of the topical use of vitamin A acid preparations is the high level of skin irritancy which follows their application. The abrasive effect of the use of such compositions often causes undesirable peeling of the skin surface epithelium and an accompanying surface roughness along with abnormal redness. Such contraindications are not only cosmetically undesirable but painfully uncomfortable for the patient. In addition, such vitamin A acid preparations are most effectively applied using an alcohol solvent system which causes its own uncomfortable burning sensation. This discomfort is particularly amplified when used on skin which has been peeled from previous uses of vitamin A acid.

Early attempts at avoiding the burning sensations caused by the use of alcohol carrier vehicles utilized preparations of vitamin A acid in cream vehicles. However, such creams were shown to be of limited usefulness, apparently because the cream binds a significant portion of the vitamin A acid, resulting in a system with diminished activity. Additionally, emulsifiers which are formulated into the creams frequently contribute to acne formation.

Other attempts at overcoming the undesirable side effects of vitamin A acid treatment utilized derivatives of vitamin A such as the various fluorinated forms of the acid as well as the limited number of the acid's amides and esters disclosed in U.S. Pat. Nos. 4,654,354, 4,395,575, 4,335,248, 4,304,787, 4,299,995, 4,231,944, 4,216,312, 4,214,000, 4,194,007, 4,171,318, 4,129,662, 4,126,699, 4,126,698, 4,126,697, 4,126,693, 4,055,659 and 3,984,544. Surprisingly, only a few of the many amides and esters of vitamin A acid disclosed showed any promise as agents for the treatment of skin disorders. Moreover, none were completely effective at eliminating the undesirable side effects of vitamin A treatment.

Accordingly, it is a principal object of the present invention to provide an improved methodology and associated pharmaceutical composition for therapeutically retarding and reversing the effects of skin photoaging and for the treatment of acne and other dermatological disorders without the abrasive and irritating characteristics of known treatments. It is a further object of the present invention to provide an effective skin treating composition which avoids the use of alcohol as a delivery solvent while maintaining its activity as a pharmaceutical preparation. It is an additional object of the present invention to provide a skin treatment methodology that accounts for variations in skin type so that a skin care regimen can be effectively maintained.

SUMMARY OF THE INVENTION

Generally stated, the present invention accomplishes these and other objectives by providing a method and associated pharmaceutical compositions provided for topical application to the skin which are particularly effective in the treatment of skin disorders without the significant side effects commonly associated with vitamin A and vitamin A acid treatments. More particularly, the present invention provides a preparation which is useful for reversing the effects of skin aging as well as for the treatment of acne. The invention is based upon the discovery that appropriately formulated and applied vitamin A propionate compositions unexpectedly exhibit unusually high skin regenerative activity without the associated side effects of other derivatives of vitamin A.

More particularly, the pharmaceutical preparations of the present invention utilize an aqueous based carrier to deliver therapeutically effective amounts of vitamin A propionate to the skin. These compositions are prepared in accordance with the teachings of the present invention utilizing known techniques for the preparation of aqueous based homogeneous systems containing oil soluble solutes. Though any pharmaceutically acceptable surfactant capable of micellizing vitamin A propionate may be used in the preparation of the aqueous carrier, sorbitan sesquioleate is preferred because of its demonstrated lack of side effects. Sorbitan sesquioleate is non irritating and does not promote acne formation. In addition, thickening agents suitable for use in dermatological applications may be added to aid in the application and handling of the preparation of the present invention. Other non-irritating additives useful in prolonging the shelf life and beneficially aiding the user, such as preservatives and sunscreens, may also be present in the preparation.

An additional aspect of the present invention is an effective methodology for the topical administration of these aqueous based vitamin A propionate compositions. Unlike the prior art methods, the method of the present invention actively takes patient skin type into account as part of the treatment regimen. Because the amount of oil produced by the skin may affect the efficacy of the vitamin A propionate composition, the frequency of application of the composition will vary with skin type. Highly oil-producing skin will generally require a more frequent administration than skin that is only slightly oil-producing. Accordingly, a preliminary step that may be employed with the method of the present invention is a skin type analysis to determine application frequency. Once determined, the rate of direct, topical application is continued until the desired result are achieved.

Further objects, features and advantages of the present invention will become apparent to those skilled in the art from a consideration of the following detailed description.

DETAILED DESCRIPTION OF THE INVENTION

In a broad aspect, the therapeutic component of the preparations disclosed in the present invention is vitamin A propionate. It distinguishes itself from other derivatives of vitamin A in that it is an ester of vitamin A itself (retinol-A retinoid alcohol) and propionic acid. More specifically, vitamin A propionate has the following structure:

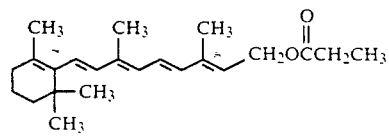

Other forms of vitamin A used topically for the therapeutic treatment of skin are derivatives of the acid form of vitamin A (retinoic acid) such as esters and amides formed from the acid. As known in the art, vitamin A derivatives in general have been shown to be dramatically unpredictable with respect to their effectiveness as skin treatments. Conversely, vitamin A propionate has clinically demonstrated unexpectedly superior properties for the treatment of skin disorders with markedly reduced side effects.

For purposes of illustration only, and without limiting the scope of the present invention, the following description will be limited to aqueous based systems for delivering vitamin A propionate topically to an area of the skin. However, it will be understood by those skilled in the art that vitamin A propionate may be used in a wide variety of applications useful for treating skin disorders and conditions responsive to inducing increased cell proliferation.

Surprisingly, the vitamin A propionate in an aqueous base of the present invention provides all of the rejuvenative benefits to the skin known to be associated with vitamin A acid without the dramatic side effects of irritation, burning, and peeling expected with such treatments. Among the positive benefits of the present invention are controlling and reversing the effects and symptoms of excess sun exposure, aging, and acne. These symptoms include such undesirable skin problems as dark blotches, wrinkles, yellowing and a leathery texture.

Moreover, when topically applied to the skin, the preparation of the present invention reverses the effects of photoaging. Thus, the dermal alterations resulting from excessive sun exposure can be corrected with an accompanying improvement in the skin appearance. The preparation of the present invention also aids in the maintenance of healthy skin and prevents the degenerative progression of skin which has been damaged but does not show clinical signs of injury. The preparations of the present invention also have wide application in the treatment of other dermatological disorders. Among these are disorders which are remedied by increasing the proliferative properties of epidermal cells such as ichthyoses, follicular disorders, benign epithelial tumors, perforated dermatoses and disorders of keratinization.

Equally surprising is the ability of the present invention to achieve these results without the serious side effects associated with the use of vitamin A acid or its known derivatives These side effects include the irritating peeling and erythema due to vitamin A acid's abrasive action as well as painful redness and swelling. Moreover, vitamin A propionate maintains its high activity when formulated into a water based lotion as disclosed herein. This has the added benefit of eliminating the burning sensations which commonly accompany the application of vitamin A acid in the prior art alcohol based carriers.

The therapeutic properties of the vitamin A propionate of the present invention are especially surprising in light of the absence of similar properties in other derivatives of the alcohol form of vitamin A. Other esters of vitamin A obtained from, for example, palmitic acid and acetic acid do not have the therapeutic advantages found with vitamin A propionate when used as disclosed herein. Vitamin A palmitate, the most common internally administered form of vitamin A and a component found in externally applied lotions, is ineffective for treating photoaged skin and acne. Presumably the molecule is so large it is not able to transdermally reach the necessary part of the skin for activity. Similarly, vitamin A acetate is too small molecularly and therefore easily recrystallizes from any solution. The inability of the acetic acid ester to stay in solution makes it unsuitable for pharmaceutical applications. Conversely, the propionic ester of vitamin A or vitamin A propionate is the appropriate molecular weight and configuration to both remain in a stable solution and to be transdermally delivered to a site where it is active.

In addition to its favorable solubility and delivery properties, when applied topically in an aqueous based carrier in accordance with the teachings of the present invention, vitamin A propionate unexpectedly provides all the benefits of vitamin A acid but minimizes the negative side effects. Users of vitamin A propionate in the aqueous based carriers of the present invention experience no significant burning sensations during application. What is more, the preparations are non-irritating and their use results in only minimal dermal peeling and erythema. In addition, use of the preparations disclosed herein results in a more unique and noticeable skin smoothness with a healthy appearing rosy hue without the irritating red associated with the harsh abrasiveness of vitamin A acid containing composition.

The vitamin A propionate preparations of the present invention may be prepared using pharmaceutically acceptable water soluble vehicles for micellizing oil soluble solutes. Non-ionic surfactants and emulsifiers are suitable for maintaining the vitamin A propionate in emulsion in a water phase. For example, emulsifiers which are esters of sorbitol, ethers of sorbitol, esters of glycerin, ethers of glycerin or from the sorbitan sesquioleate series are particularly applicable for providing a stable emulsion of vitamin A propionate.

Though not essential to practice the present invention, the handling characteristics of the aqueous based carrier system of the present invention can be varied by the addition of thickening agents which add body to the composition and are capable of increasing the viscosity of the aqueous base. Any pharmaceutically acceptable and water soluble thickener which is stable in the presence of vitamin A propionate is suitable for this application. Carboxypolymethylenes are particularly useful as a thickening agent. The amount of thickening agent used depends upon the desired consistency and viscosity. Preferably, the compositions produced in accordance with the teachings of the present invention will be opaque creams which are easily applied to the skin. Those skilled in the art will appreciate that carrier systems containing thickening agents with viscosity characteristics which are dependent upon the system pH may require a pH adjustment using NaOH or HCl.

Similarly, it is also contemplated as being within the scope of the present invention to increase the shelf life of the vitamin A propionate compositions of the present invention by adding preservatives in amounts which do not alter the safety and efficacy of the preparation, but preserve its usefulness Any compatible preservative which is pharmaceutically acceptable is appropriate for this application. Preferred preservatives are butylated hydroxytoluene, methyl paraben, propyl paraben, ethyl paraben, and phenoxyethanol.

Where desired, it is also contemplated as being within the scope of the present invention to add sunscreens or other additives commonly used in externally applied lotions. These are appropriate components for the vitamin A propionate preparation of the present invention and have the additional benefit of protecting the skin being treated from further sun damage Among the additives preferred are paraaminobenzoic acid, 4 (dimethylamino) benzoic acid, extracts of the aloe vera plant, and common lotion additives such as sodium PCA, sodium lactate, urea, nicotinamide, fructose. (Avialable commercially in a mixture as LACTIL.)

The vitamin A propionate emulsion of the present invention may be prepared by any method known in the art for forming emulsions of oil soluble solutes in water. An exemplary method comprises mixing the appropriate amount of water, thickening agent, and a single emulsifier or surfactant and heating to about 170 F. A second heated system comprising vitamin A propionate, one or more suitable emulsifiers or surfactants, preservatives, and, where desirable, sunscreen or other additives added with constant stirring at 170. F. is also prepared. The next step consists of mixing the two systems together with constant stirring and then allowing the mixture to cool slowly. When the combined mixture cools to approximately 120° F. aloe vera extract and LACTIL can be added if desired. If necessary, the viscosity of the system can be adjusted using a 10% solution of NaOH.

The effectiveness and success of the topical application of the vitamin A propionate composition in accordance with the teaching of the present invention is influenced by the skin type being treated. If the skin is quite oily it will dilute the vitamin A propionate . . cause a less effective result. If the skin is dry with th . . lication of a low oil production, the vitamin A prop nate will penetrate rapidly into the skin causing a quickened response. Along these lines, atmospheric conditions are also influential in the effectiveness of the vitamin A propionate. If the humidity is low, the skin is not well hydrated and thus is more susceptible to the effects of the vitamin A propionate composition. In order to determine the appropriate frequency of application, the method of the present invention has been developed to determine the skin type to the vitamin A propionate user as a factor in the treatment modality. This method allows the user to determine the degree to which the skin produces oil and hence to determine the appropriate frequency of application.

In accordance with the teaching of the present invention, a method for visualizing the degree to which the skin produces oil is utilized to determine the frequency of application of the vitamin A propionate composition. The skin analysis is preferably accomplished by applying an oil absorbent material to a clean and dry area of the skin, such as the forehead. After a period of time which is adequate to absorb sufficient skin oil for measurement, the oil absorbent material is removed. This time period is normally on the order of one hour for most individuals. The oil absorbent material is then developed by pressing it against or allowing it to come in contact with an oil absorbing or oil complexing dye. In the alternative, the oil absorbent material may be pressed against a darkened surface where the area absorbed by the oil is visualized through the transparency developed by the oil. The resulting visually developed absorbent material is then referenced to absorbent patterns which are known to be characteristic of dry skin, combination skin (moderately oily) and oily skin, in order to determine skin type and treatment.

Once skin type has been determined, the recommended course of treatment for each of the above types of skin using the vitamin A propionate composition of the present invention is as follows:

Dry skin—apply the preparation every third night for a week, then every other night for a week, and finally every night. During periods of dry weather, use a humidifier. Combination skin—apply the preparation every other night . for a week or ten days, then every night. Oily skin—apply the preparation every night. After becoming accustomed to the treatment, use it in the morning as well. It should be noted that because vitamin A propionate accelerates the skin turnover time, the thick protective barrier is less effective. Consequently, ultraviolet radiation is more damaging. To avoid this, the use of a sunscreen of SPF 15 or greater is strongly recommended.

Preferred materials for use in the analysis of skin type may be any pharmaceutically acceptable material with oil absorbing properties. In particular, filter tape has been found to be a safe and effective agent for collecting oil from skin. A convenient method for delivering the oil absorbing material to the skin is to apply it to an adhesive backed tape or patch. The adhesive is also able to function as a means for adhering the patch to the skin.

The oil absorbing dye may be any dye which is safe to handle, will preferentially complex skin oil and is able to be visually differentiated from the oil absorbent in its complexed form. Suitable dyes are known to be oil red 0.

In order to more fully describe the invention and its superior properties for the treatment of skin disorders, the following examples are offered. It is understood that these examples do not limit the scope of the invention. An exemplary vitamin A propionate composition is prepared as follows.

EXAMPLE 1

Preparation of a Water Based Composition Useful in Treating Skin Disorders a. Add 28.3 grams of a 1.5 wt% solution of Carbopol (a carboxypolymethylene thickener) to 55.85 grams distilled or deionized water and 5.0 grams of EG-1, an ethoxylated ether of glycerine. Heat the solution to 170° F.

b. Add the following components together, mixing well during addition:
- 1.2 grams vitamin A propionate
- 2.0 grams Liposorb SQO (a sorbitan sesquioleate)
- 1.0 grams Lipo L-20 (a polysorbate 20)
- 0.05 grams butylated hydroxytoluene
- 1.0 grams padimate 0 (4 (dimethamino) benzoic acid)
- 0.5 grams undebenzophene Heat the system to 170° F.

c. Add the two systems together while agitating well. Allow the mixture to cool while continuing to mix.

d. When the mixture temperature cools to 120° F. and while stirring, add 5.0 grams of extract of the aloe vera plant and 0.1 grams LACTIL.

e. Adjust the viscosity of the mixture to 24,960 cPs as indicated by a Brookfield Viscometer using the F-spindle at 3 rpms and at 77° F. by the addition of 10% NaOH solution. This will bring the pH to between 5.0–5.5 and produce an opaque, creamy lotion.

The efficacy of the composition of the present invention was determined as follows.

EXAMPLE 2

Guinea Pig Epidermal Proliferation Study

The vitamin A propionate formulation described in example 1 was applied to the right ear of ten guinea pigs. The formulation without the vitamin A propionate was applied to the left ear as a control. The applications were continued for 14 days, after which the guinea pigs were injected intraperitoneally with radioactive 3H-Thymidine (10 micro Curies—specific activity. 1.9 C/mM) and after one hour sacrificed. The ears were processed for auto-radiography following the method of Weinstein and Frost (J Invest Dermatol 50:254–259, 1968). The tissue was analyzed using light microscopy at 100X. The number of epidermal cells incorporating the precurser of DNA, the radioactive thymidine, reflects the turnover of the skin and normally runs at about 5% of the cells. The guinea pig ears treated with the vitamin A propionate formulation showed 22.5% of the cells replicating, a substantial increase over the control ear replicating rate of 6.2%.

EXAMPLE 3

Computer Imaging for Contour Analysis

Ten human subjects applied the formulation described in example 1 daily for one month to the forehead skin. A contour analysis which provides quantitative values and three-dimensional graphic representations of the skin surface within 20 microns was performed on all subjects before and after the one-month treatment. The skin smoothness and the wrinkle depth was recorded and compared to their pre-treatment value. There was a 18.2% improvement in the depth of superficial fine lines.

EXAMPLE 4

Transepidermal Water Loss

The use of the rate of transepidermal water loss (TEWL) is a recognized means for measuring the stratum corneus thickness. A normal 14 cell layer thick stratum corneum effectively blocks insensible water loss through the skin into the environment. TEWL increases when the top layers of the stratum corneum are reduced in thickness. Irritants other than vitamin A acid and its derivatives are known to increase the stratum corneum thickness as a normal defense mechanism. Such known irritants include detergents, ultraviolet radiation and chemical burns. Ten subjects were treated with the vitamin A propionate formulation of example 1 for fourteen days on their right arm to study its effects on TEWL. A control consisting of the preparation without the vitamin A propionate was applied to the left arm. The TEWL was measured both before and after the treatment period following the method of Baker and Kligman (J Invest Dermato 96:441-452, 1967). The result was a 22% increase in the transepidermal water loss at the vitamin A propionate site relative to the control site.

EXAMPLE 5

Clinical Observations of Vitamin A Propionate Users at Seven Skin Treatment Clinics a. Over 370 human users of the vitamin A propionate described in example 1 have reported favorable results. About one-half were treated for acne complexions and the other half for extensive sun damage. Of those treated with impacted pores for an acne condition, there was a significant evacuation of the buildup debris and significant complexion clearing. In users with clinical symptoms of sun damage, there was a rejuvenation of the photoaged skin resulting in smoother skin and diminished fine lines.

b. Approximately 200 people of Black, Hispanic, or Oriental origin with a median age of 30 participated in a trial using the vitamin A propionate of example 1. Most of the users reported improvement in 4-6 weeks. The only adverse reactions followed harsh scrubbing practices prior to use.

c. In another study 75 users of the example 1 formulation reported noticeable improvements and a high degree of satisfaction in the product. The ages ranged from 18 to 60 with 10 participating in an acne control program and the remainder in a skin rejuvenation program.

d. Fifty users ranging in age from 15-50 used the product of example 1 in a trial. With the exception of three clients who experienced some itching there was general satisfaction with the vitamin A propionate. They noticed increased skin tone and diminishing facial lines.

e. Another clinic with approximately 70% acne clients between the ages of 16 and 24 reported successful results in 6-8 weeks of treatment. The increased clearing was especially evident in clients who had open and closed comedones. Clients in the 32-45 age group from this same clinic reported favorable skin rejuvenation in 4-6 weeks.

f. Approximately 40 users of the vitamin A propionate of example 1 in the 30-60 age range reported overall sastisfaction. Many reported light peeling and liked the fact that the product did not over dry the skin. Results were reported in 3-4 weeks. Four users reported slight darkening of the skin but did not discontinue the use because they liked the product.

g. In another study, 30 users in the 16-62 age range reported a high degree of satisfaction in the example 1 formulation of vitamin A propionate. In 3-4 weeks the users reported better and softer skin tone with diminished crow's feet. The greatest improvement is seen in the 35-62 year olds in reducing the visible signs of aging.

I claim:

1. A topically applied, alcohol-free pharmaceutical composition for rejuvenating skin comprising:
   from about 0.1% to 4.0% by weight vitamin A propionate;
   from about 1.0% to 5.0% by weight non-ionic surfactant;
   from about 0.1% to 1.0% by weight at least one pharmaceutically acceptable preservative; and from about 50% to 90% by weight water.

2. The composition of claim 1 wherein said non-ionic surfactants are selected from the group consisting of sorbitol esters, sorbitol ethers, glycerine esters and glycerine ethers.

3. The composition of claim 1 wherein said non-ionic surfactants are a mixture of polysorbate 20, a polyethylene oxide ether of glycerin, and sorbitan sesquioleate.

4. The composition of claim 1 wherein said aqueous based carrier further comprises a pharmaceutically acceptable thickening agent.

5. The composition of claim 4 wherein said thickening agent is carboxypolyethylene.

6. The composition of claim 5 further comprising a sufficient quantity of 10% NaOH solution to cause the viscosity of the composition to be between 23,000 and 26,000 cps.

7. The composition of claim 1 wherein said pharmaceutically acceptable preservatives are selected from the group consisting of butylated hydroxy toluene and undebenzophene.

8. The composition of claim 1 wherein said aqueous based carrier further comprises from about 5.0% to about 40% aloe.

* * * * *